United States Patent [19]

Marion

[11] Patent Number: 5,088,368
[45] Date of Patent: Feb. 18, 1992

[54] CUTTING DEVICE FOR MATERIALS SUCH AS GAUZE

[76] Inventor: Louis Marion, Vieux Bourg de Condamine, Saint Victor Sur Loire, France

[21] Appl. No.: 443,704

[22] Filed: Nov. 29, 1989

[30] Foreign Application Priority Data

Dec. 1, 1988 [FR] France ................. 88 16489

[51] Int. Cl.$^5$ ............ B26D 1/62; B23D 25/12
[52] U.S. Cl. ............................ 83/348; 83/346; 83/671; 493/357; 493/960
[58] Field of Search ............ 83/37, 298, 346–348, 83/671, 668, 917; 493/357, 360, 444, 960

[56] References Cited

U.S. PATENT DOCUMENTS

| | | | |
|---|---|---|---|
| 1,909,027 | 5/1933 | Valentine . | |
| 3,800,640 | 4/1974 | Barrie | 83/37 |
| 3,952,637 | 4/1976 | Lambert et al. | 93/58.2 R |
| 4,597,748 | 7/1986 | Wolf | 493/357 X |

FOREIGN PATENT DOCUMENTS 1427560 3/1976 United Kingdom .
2099306 3/1982 United Kingdom .

*Primary Examiner*—Steven C. Bishop
*Attorney, Agent, or Firm*—Eckert Seamans Cherin & Mellott

[57] ABSTRACT

A cutting device for materials such as gauze is provided by a circular knife having a cutting edge suitable for making an incision in several sizes of swabs. The knife is rotatable in correspondence with a succession of swabs moving along a path. The swabs have a folded edge in a direction of movement. A counter roller is elastically biased against the knife and disposed for passage of the moving swabs therebetween. A Y-shaped incision extending from the folded edge is made in the moving swabs by the knife.

4 Claims, 1 Drawing Sheet

CUTTING DEVICE FOR MATERIALS SUCH AS GAUZE

BACKGROUND OF THE INVENTION

1. Field of the Invention

The invention relates to a cutting device for materials such as gauze. The invention further relates to the technical fields of handling products in strips and means for cutting these products.

2. Prior Art

Gauze swabs are used to bandage wounds, to absorb blood, or to protect and isolate wounds. The swabs are generally made on machines which, using spools, separate the strips which are to be formed into the swabs, then make a fold or folds in the strips, stack the swabs and finally put them into bags.

For certain applications, such as treatment of patients having tracheotomies, there is an advantage in making an incision in the folded swab to enable a by-pass catheter to pass through. Some machines currently on the market make this incision; however, they do not have a large output due either to the way the cutting tool is designed or because they do not operate continuously. Also, the shape of the incision and the power train of the machine do not always allow several sizes of swabs to be processed.

It is an object of the invention to continuously produce an incision in folded swabs of different sizes. The shape and dimensions of the incision will allow catheters and other therapeutic means having cross-sections of different sizes to pass through.

SUMMARY OF THE INVENTION

With this in mind and according to a first characteristic, the invention comprises a circular knife with at least one cutting edge sized to produce an incision adapted to several sizes of swabs, the knife being rotated as a function of the passage of the folded swabs, an elastic positioning roller being mounted in opposition to the knife and acting as a counter tool.

According to another characteristic, the cutting device is integrated into a machine and is disposed between a swab folding station and a swab packaging station, above a set of swab conveyor belts.

According to another characteristic, the incision is Y-shaped, the leg of the Y extending from a folded edge of the swab substantially into a central part where the two arms of the Y are defined.

According to another characteristic, the cutting edge of the circular knife is defined on a ring mounted on a cylinder with means for lengthwise and crosswise adjustment with respect to the set of conveyor belts.

In another characteristic, the elastic positioning roller or counter tool which is pressed against the knife can be retracted to enable passage of the swabs without incisions.

These characteristics and others will be made apparent from the following description.

BRIEF DESCRIPTION OF THE DRAWINGS

There are shown in the drawings the embodiments of the invention that are presently preferred. It should be understood, however, that the invention is not limited to the precise arrangements and instrumentalities shown in the drawings, wherein.

DETAILED DESCRIPTION OF THE PREFERRED EMBODIMENTS

Figure 2:
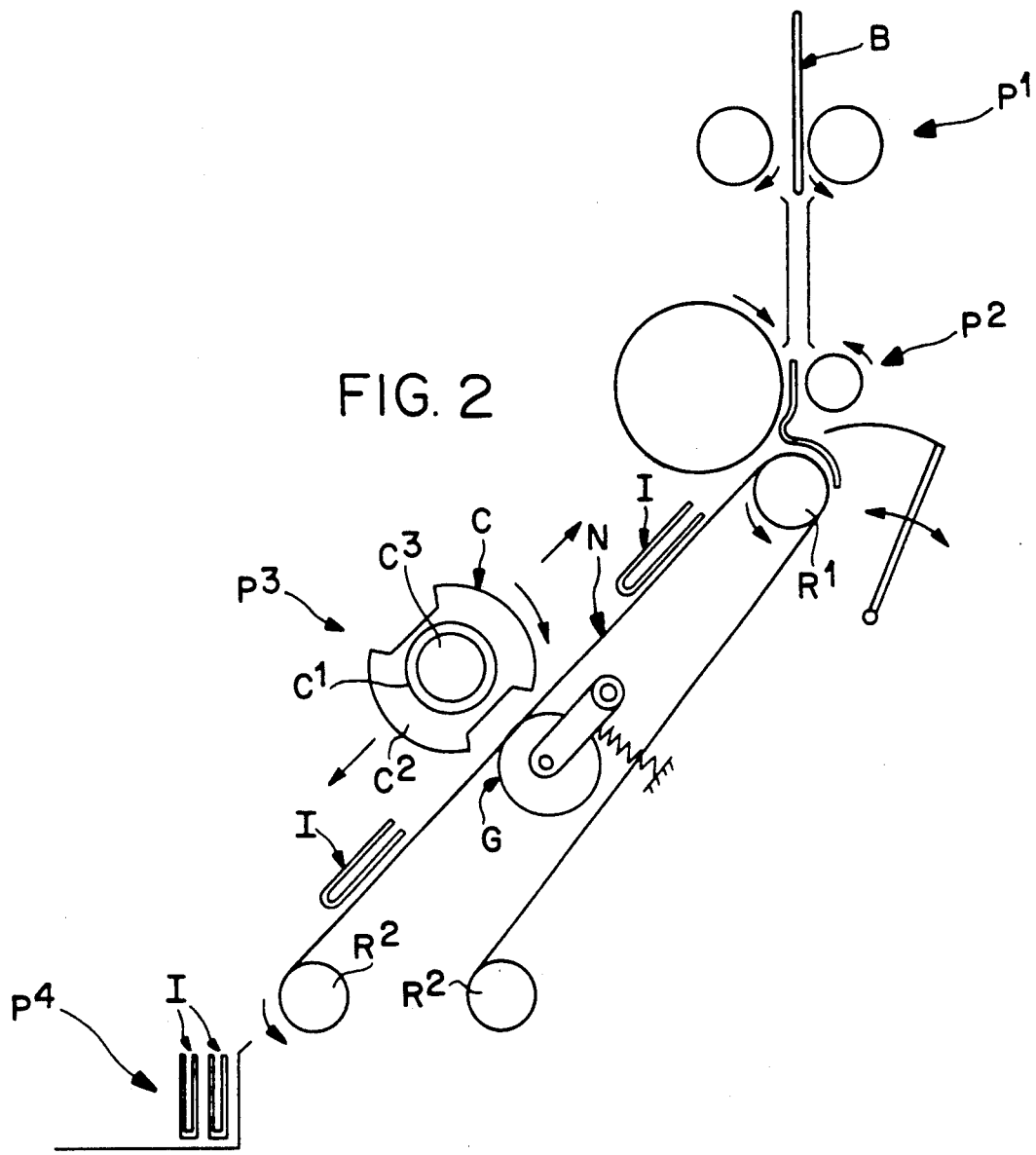
FIG. 2 is a schematic view showing the cutting device integrated into a machine between a swab folding station and a swab packaging station. The object of the invention will become more apparent from the following non-limiting description when considered in conjunction with the accompanying figures of the drawing.
Figure 1:
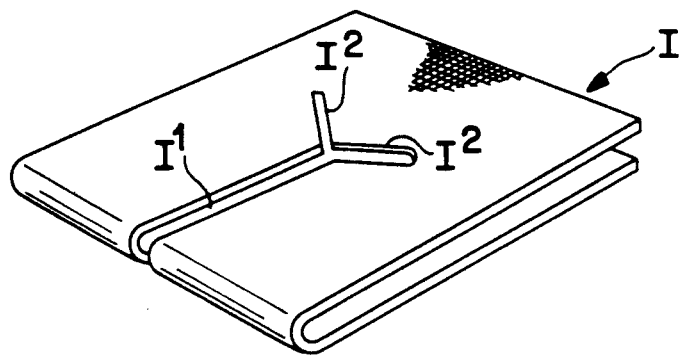
FIG. 1 is a perspective view of a swab with an incision according to the invention.

As shown in FIG. 2, a gauze strip (B) is suitably cut to make individual swabs (I) at a cross-cutting station (P1). The swabs are folded at a swab folding station (P2), which can have several folding assemblies. Incisions are made in the folded swabs at station (P3), and the swabs are delivered to swab packaging station (P4). In a known manner, the station (P3) comprises a set of conveyor belts (N) looped around rolls (R1,R2).

Mounted approximately in a central location above the set of belts (N) is a circular knife (C) which comprises a ring (C1) with at least one cutting edge (C2). Preferably, several knives are mounted coaxially in order to simultaneously incise several tracks of swabs across the width of the set of belts. The ring (C1) is mounted on a cylinder (C3) which is rotatable in a support which is positioned with respect to the cross-cutting station (P1).

The circular knives are adjustable transversely relative to the belts to accommodate more than one size of the swabs. For this purpose, the cutting edges can always be positioned above a space between two belts. Similarly, the circular knives are longitudinally adjustable along a length of the belts as a function of the size of the swabs so that the cutting edges can be adjusted to penetrate at a desired position along a length of the folded swabs.

The invention further comprises a counter tool which includes one or several rollers (G) mounted within the loops of the set of belts and which is elastically biased against the knives. If an incision is not desired in the swabs passing on the set of belts, the rollers can be retracted away from the knives by a suitable retraction means, such means being well know in the art.

In a preferred embodiment, the cutting edges are adapted to produce a Y-shaped incision having a leg (I1) extending from a folded edge of the swab and arms (I2) defined in a central part of the swab.

The cutting device according to the invention may be independent of any other machine, in which case a folded swab distribution station is provided upstream of the cutting device, and a station for receiving swabs with incisions is provided downstream of the cutting device.

The invention has advantages including permitting continuous production of incisions in swabs, being adaptable to produce incisions having various shapes and sizes, and permitting incisions to be produced in various sizes of swabs.

I claim:

1. A cutting device for materials such as gauze, comprising:
    a circular knife having at least one cutting edge, the knife being rotatable in correspondence with a succession of swabs moving along a path, the swabs having a folded edge disposed toward a direction of movement; and, a counter roller which is elastically biased against the knife and disposed for passage of the moving swabs between the counter roller and the knife, whereby an incision is made in the moving swabs, the incision being Y-shaped and defining a leg extending from the folded edge to a central part of the swab, the incision further defining arms extending from the leg at the central part.

2. The cutting device according to claim 1, wherein the circular knife is transversely and longitudinally adjustable with respect to the path of the moving swabs.

3. The cutting device according to claim 1, wherein the counter roller is retractable from the knife to permit passage of swabs without incisions.

4. The cutting device according to claim 1, wherein the device is integrated into a machine and disposed along a set of swab conveyor belts between a swab folding station and swab packaging station of the machine.